United States Patent
Schmitt et al.

(10) Patent No.: US 12,090,259 B2
(45) Date of Patent: *Sep. 17, 2024

(54) WALL BOX FOR HEMODIALYSIS INTERFACE

(71) Applicant: EVOQUA WATER TECHNOLOGIES LLC, Pittsburgh, PA (US)

(72) Inventors: Steven M. Schmitt, Muskegon, MI (US); Garry O. Miller, Eden Prairie, MN (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/143,580

(22) Filed: May 4, 2023

(65) Prior Publication Data

US 2023/0270924 A1 Aug. 31, 2023

Related U.S. Application Data

(63) Continuation of application No. 16/789,492, filed on Feb. 13, 2020, now Pat. No. 11,679,185.

(51) Int. Cl.
*A61M 1/16* (2006.01)

(52) U.S. Cl.
CPC .... *A61M 1/1668* (2014.02); *A61M 2205/0205* (2013.01); *A61M 2209/084* (2013.01)

(58) Field of Classification Search
CPC ........ A61M 1/1668; A61M 2205/0205; A61M 2209/084; A61M 1/14; A61B 50/10; A61B 50/18; A61B 2050/105
See application file for complete search history.

(56) References Cited

U.S. PATENT DOCUMENTS

| | | | | |
|---|---|---|---|---|
| 3,934,605 | A | * 1/1976 | Legris | F16L 37/26 285/125.1 |
| 8,460,544 | B2 | 6/2013 | Volker | |
| 2012/0031502 | A1 | * 2/2012 | Randall | A61M 1/1682 137/15.01 |
| 2015/0000758 | A1 | 1/2015 | Randall et al. | |
| 2015/0083647 | A1 | 3/2015 | Meyer et al. | |
| 2018/0021500 | A1 | 1/2018 | Gerber et al. | |
| 2018/0361046 | A1 | 12/2018 | Moretti et al. | |
| 2019/0186110 | A1 | 6/2019 | Taweh | |

* cited by examiner

*Primary Examiner* — Sarah Al Hashimi
*Assistant Examiner* — Nhu Q. Tran

(57) ABSTRACT

The present invention is directed to wall box for hemodialysis interface having two isolated zones. The first zone is a clean interface zone having sources of purified water and dialysis fluids. The second zone is a waste interface zone comprising waste connectors and a waste drain.

10 Claims, 12 Drawing Sheets

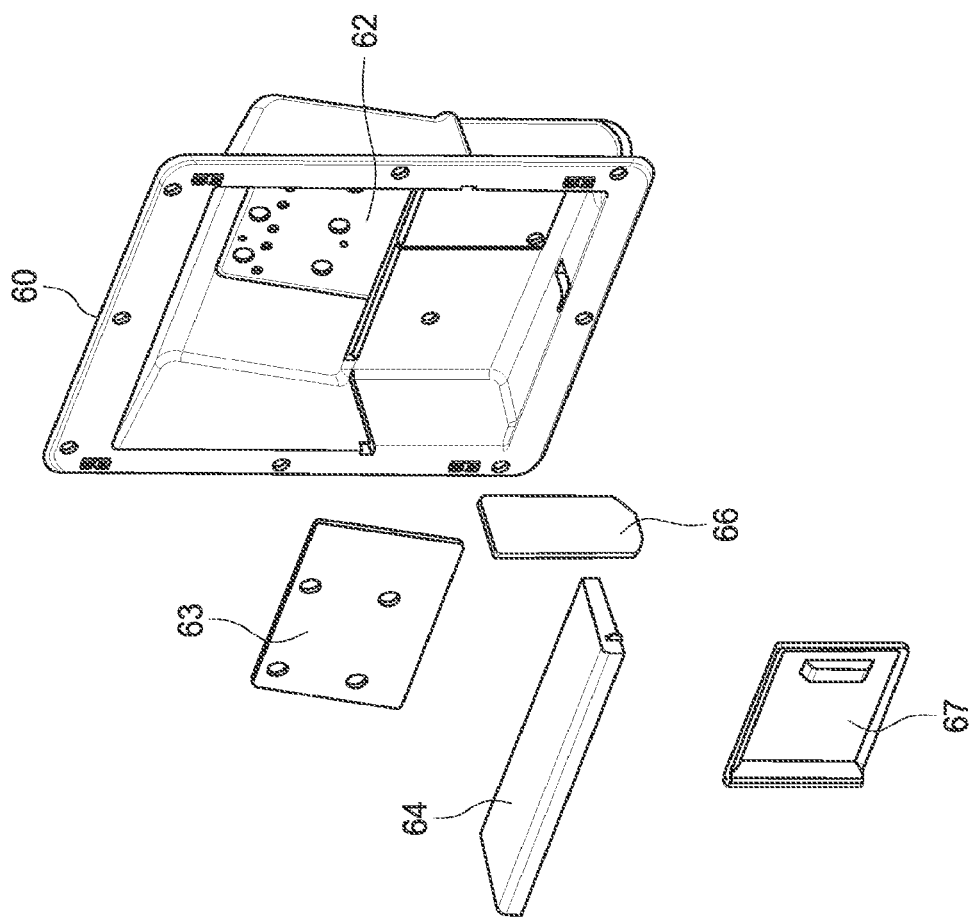
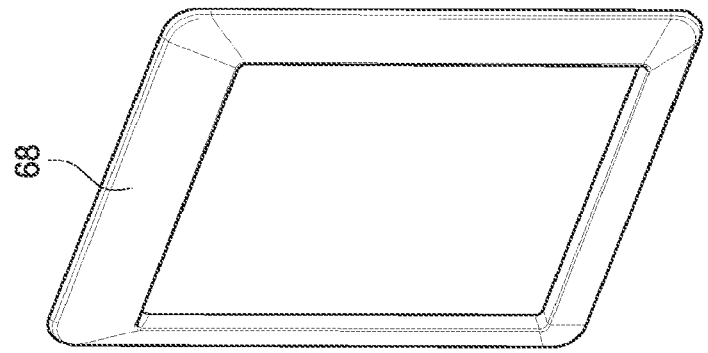
FIG. 6

WALL BOX FOR HEMODIALYSIS INTERFACE

PRIORITY CLAIM

This application claims priority to and benefit of U.S. Provisional Application with Ser. No. 62/808,915 filed Feb. 22, 2019, entitled WALL BOX FOR HEMODIALYSIS INTERFACE, which is herein incorporated by reference in its entirety.

SUMMARY OF THE DISCLOSURE

This disclosure provides a wall box for a hemodialysis machine interface with, for example, reverse osmatic water loops, bicarbonate solution loops, and acid solution loops. In some embodiments the wall box has two distinct zones to isolate or separate clean zones and connections from waste or dirty zones and connections.

Some specific embodiments of this disclosure include, for example, i) a snap in faceplate to cover valve mounting hardware, ii) a screw fastened escutcheon to cover mounting hardware for PEX connective RO loops, iii) a door in the lower right quadrant where the hemodialysis' machine waste is dispensed, (to prevent inadvertent splashing which has been known to cause cross-contamination from drain waste to hemodialysis staff and patients, or iv) a snap on bezel to cover the mounting hardware of the wall box (preventing rusting the mounting hardware and provides an aesthetic piece).

In some embodiments of this disclosure, the wall box uses snap together components which make it simple to assemble and disassemble for terminal cleaning if desired. In other embodiments the wall box is impregnated with an anti-microbial product to inhibit bacterial growth.

Other embodiments of this disclosure include, but are not limited to, a wall box for hemodialysis interface comprising at least two isolated zones, a first clean interface zone comprising sources of purified water and one or more dialysis fluids, and a second waste interface zone comprising one or more waste connectors and a waste drain.

In some embodiments, the first clean interface zone comprises a reverse osmosis water input and a reverse osmosis water outlet, and an inlet for one or more dialysis fluids and an outlet one or more outlet for one or more dialysis fluids.

In other embodiments, the first clean interface zone comprises one or more inlet and outlets for a bicarbonate solution, a primary acid solution, a secondary acid solution or a tertiary acid solution.

In some embodiments, the wall box comprises a molded base fitted with apertures for reverse osmosis water and one of more dialysis fluids valves, a plurality of valves or connectors, a horizontal divider separating the isolated clean interface zone from the isolated waste interface zone, a vertical divider separating a waste connector section from a waste drain section and a hinged cover enclosing the waste drain section.

In other embodiments, the wall box is impregnated with an anti-microbial product to inhibit bacterial growth.

DESCRIPTION OF THE DRAWINGS

FIG. 6 is an exploded view of an embodiment of wall of this disclosure.

DETAILED DESCRIPTION

Figure 1:
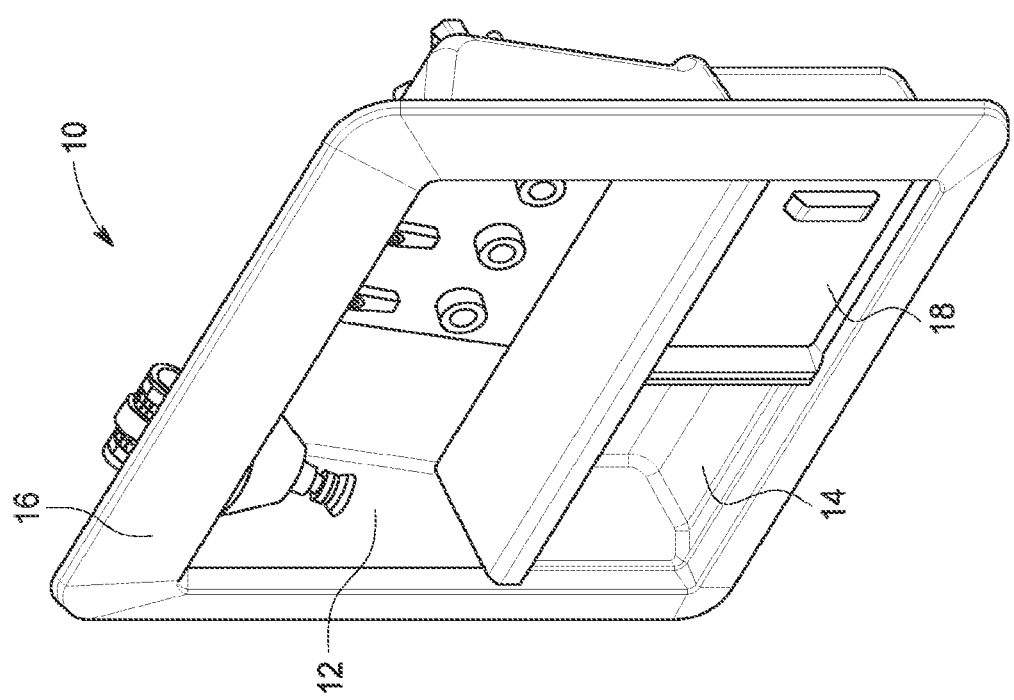
FIG. 1 is a perspective view of an embodiment of a wall box of this disclosure.

FIG. 1 illustrates an embodiment of a wall box 10 of this disclosure having an upper clean interface zone 12 and a lower waste interface zone 14. This figure also illustrates a bezel 16 that covers the perimeter of the wall box and a cover for a waste drain 18.

Figure 2:
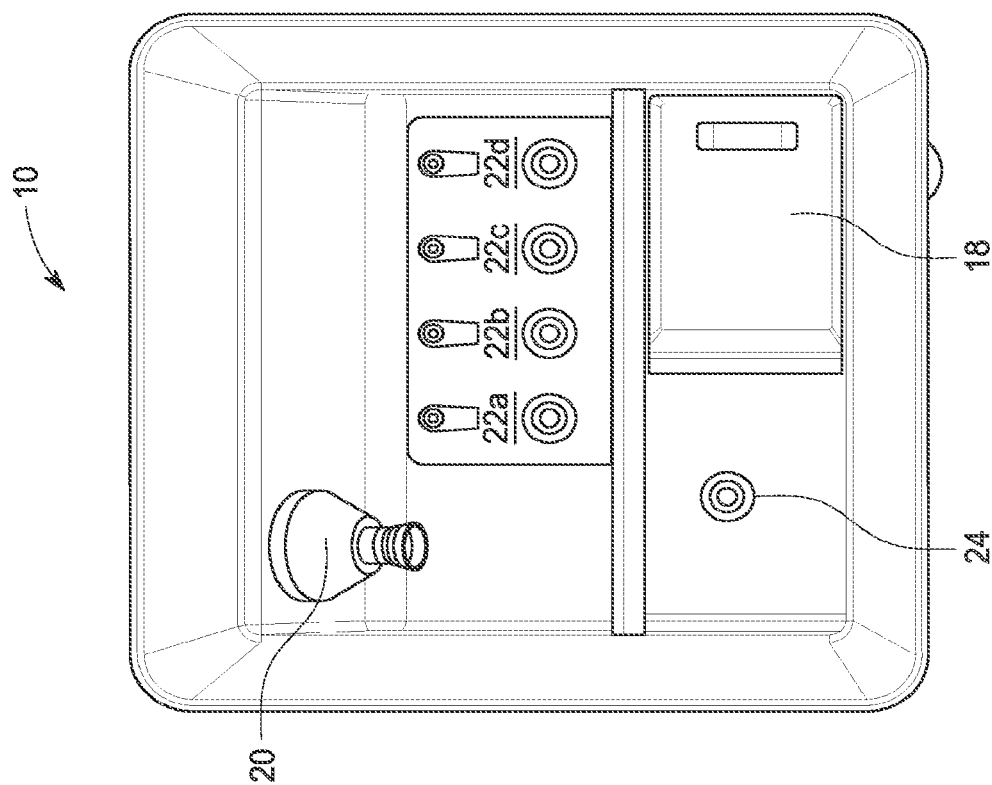
FIG. 2 is a front view of an embodiment of a wall box of this disclosure.

FIG. 2 illustrates the source of reverse osmosis (RO) water from connector and valve 20 and sources of dialysis fluids from connectors and valves 22a-22d in the clean interface zone as well as a waste connect 24 for dialysis waste and a covered compartment 18 for a waste drain in the waste interface zone. Suitable dialysis fluids include aqueous generally used for dialysis treatment including, for example, bicarbonate solutions, primary acid solutions, secondary acids solutions, or tertiary acid solutions.

Figure 3:
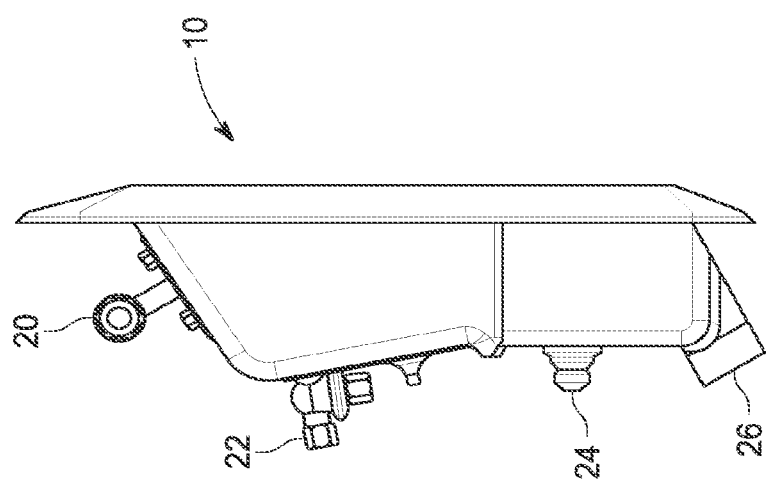
FIG. 3 is a side view of an embodiment of a wall box of this disclosure.

FIG. 3 illustrates a side exterior view of a wall box with RO water connector and valve 20, dialysis fluid connectors and valves 22, waste connector 24 and waste drain 26.

Figure 4:
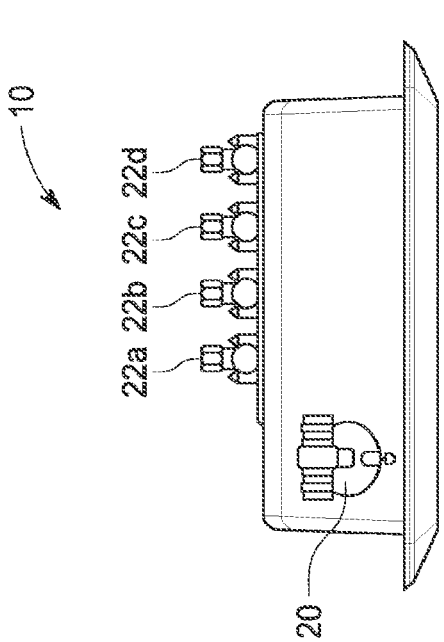
FIG. 4 is a top view of an embodiment of a wall box of this disclosure.

FIG. 4 illustrates a top exterior view of a wall box with RO water connector and valve 20, and dialysis connectors and valves 22a-22d.

Figure 5:
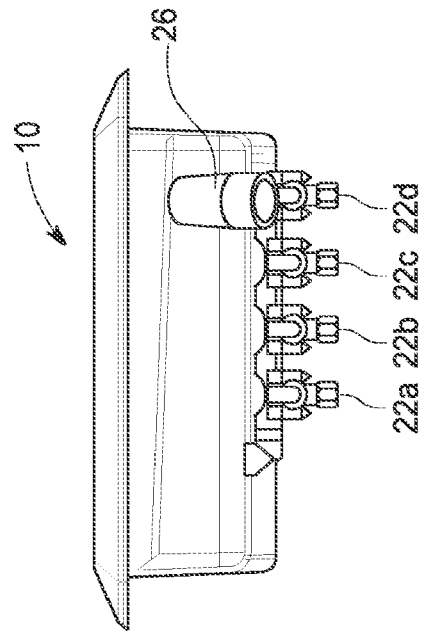
FIG. 5 is a bottom view of an embodiment of a wall box of this disclosure.

FIG. 5 illustrates a bottom exterior view of a wall box with dialysis connectors and valves 22a-22d, and waste drain 26.

FIG. 6 illustrates components of a wall box of this disclosure including molded base 60, apertures for RO water valves and connectors (not shown) and dialysis fluid valves and connectors 62, a cover plate for the dialysis fluid connectors and valves 63, a horizontal divider 64 to isolate a clean interface zone from a waste interface zone, a vertical divider 66 to isolate the waste drain (not shown), a hinged cover enclosing a waste drain compartment 67, and bezel 68.

In some embodiments, one or more of these components may be impregnated with an antimicrobial product to inhibit bacterial growth. Suitable moldable materials for making the wall box components include thermoplastic materials and thermosetting materials as well as other engineered plastics typically used for making molded components and parts. The illustrated components are readily assembled into a wall box having isolated clean and waste interface zones.

Figure 7:
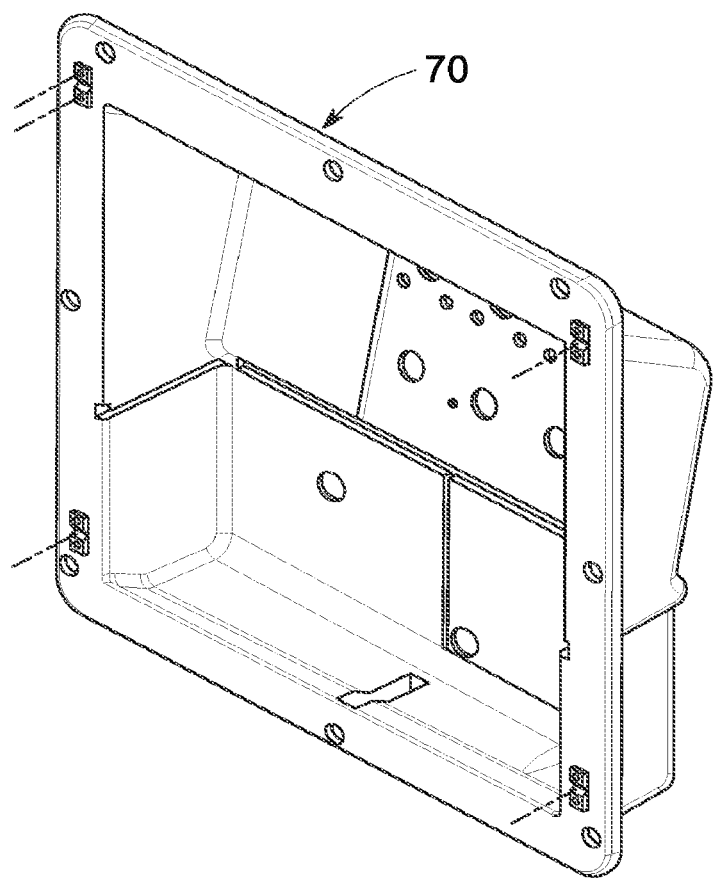
FIG. 7 is a perspective front view of an embodiment of a molded base of a wall box.

FIG. 7 illustrates a molded base 70 of a wall box of this disclosure.

Figure 8:
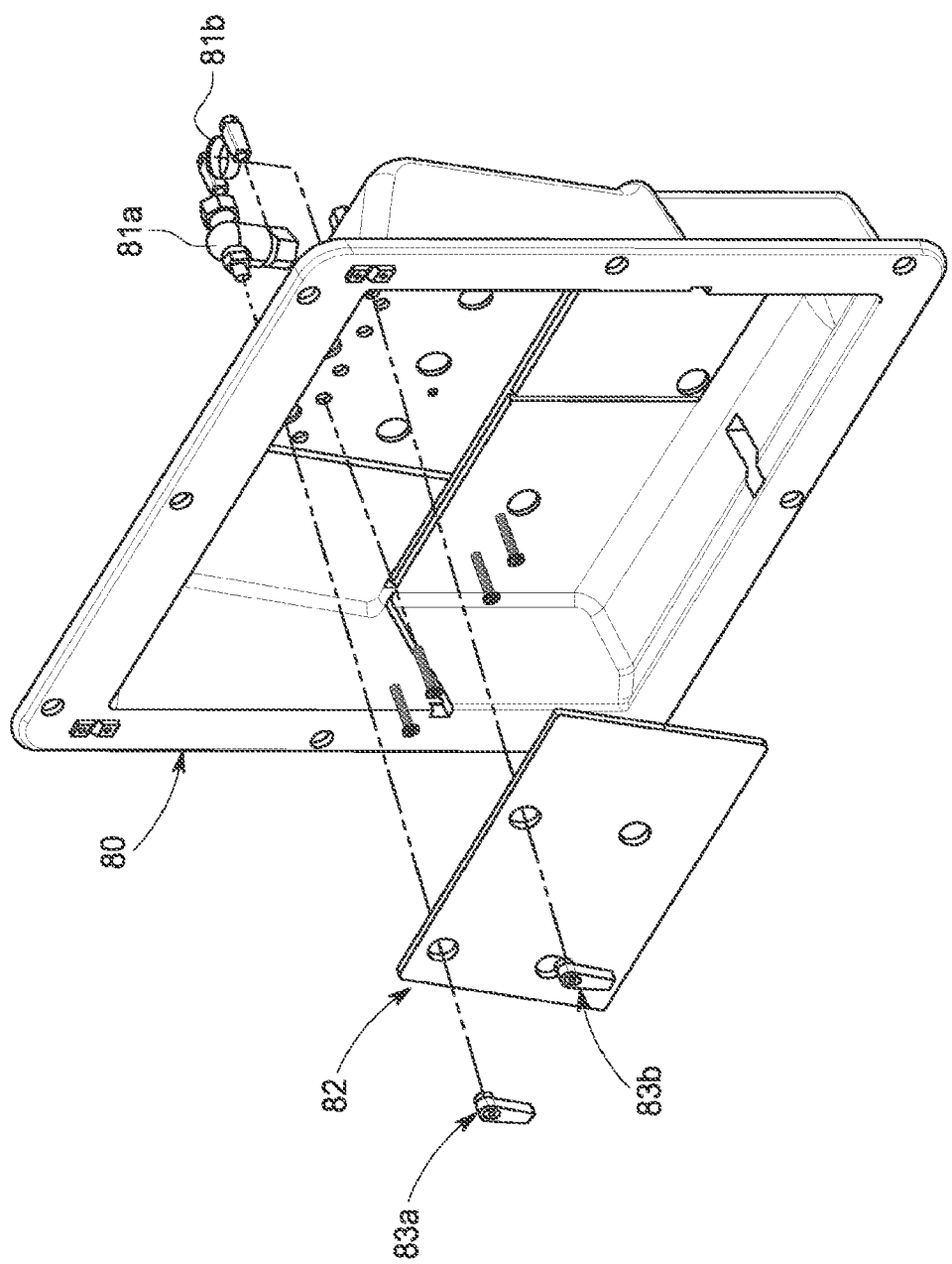
FIG. 8 is a perspective front view of an embodiment of a molded base of a wall box and a cover plate for valves or connectors.
Figure 9:
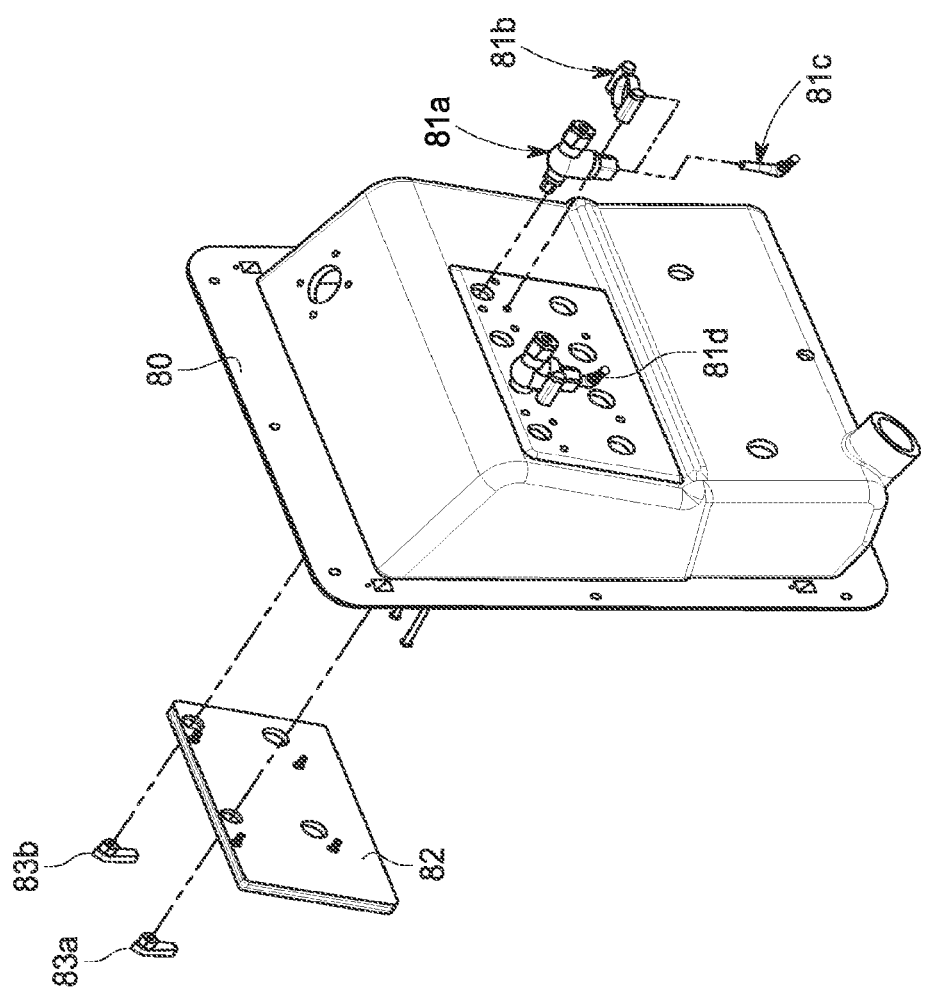
FIG. 9 is a perspective back view of an embodiment of a molded base of a wall box and a cover plate for valves or connectors.

FIGS. 8 and 9 illustrate front and back perspective views, respectively, of a molded base 80, dialysis fluid valves, connectors and fittings 81a-81d, a cover plate 82, and valve handles 83a and 83b.

Figure 10:
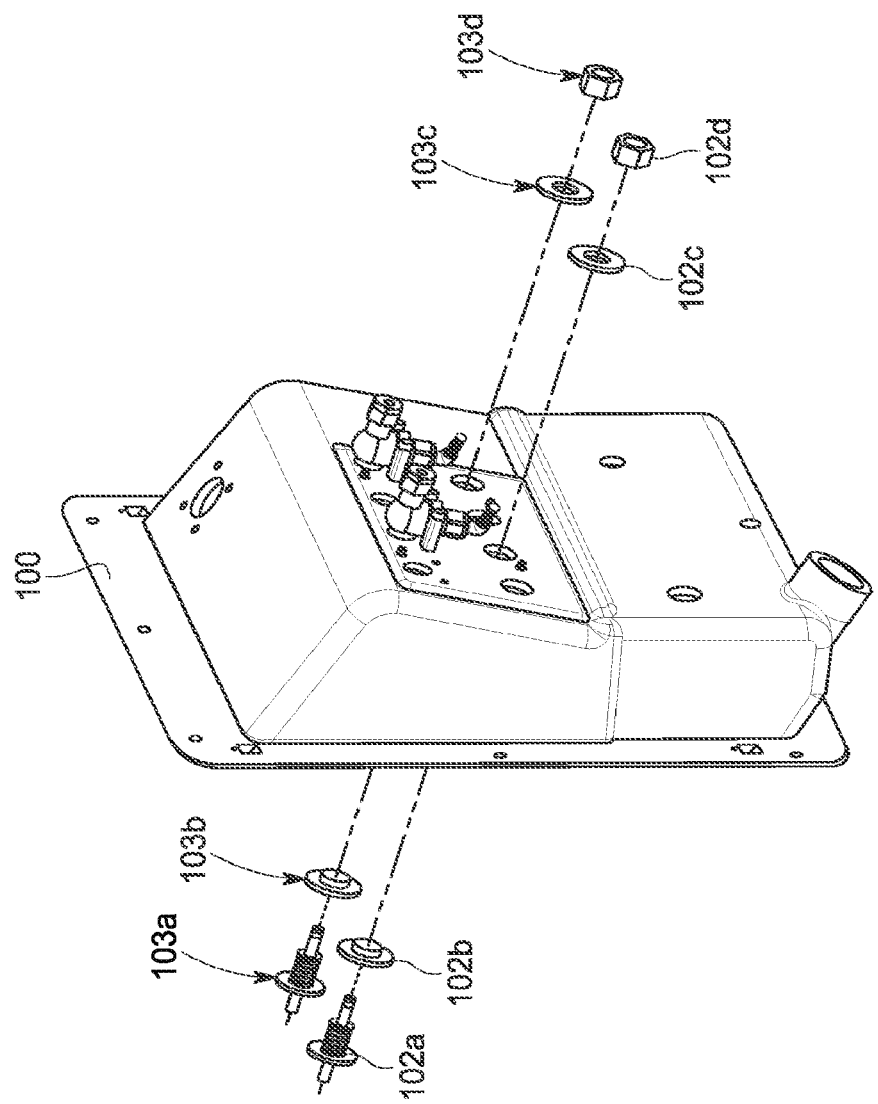
FIG. 10 is a perspective back view of an embodiment of a molded base of a wall box and valves.

FIG. 10 illustrates a back perspective of a molded base 100, and dialysis fluid connector components 102a-102d and 103a-103d. Suitable dialysis fluid connector components include, for example, generally know components for fluid handling systems using PEX, PTFE, or other generally used fluid handling tubing or conduits.

Figure 11:
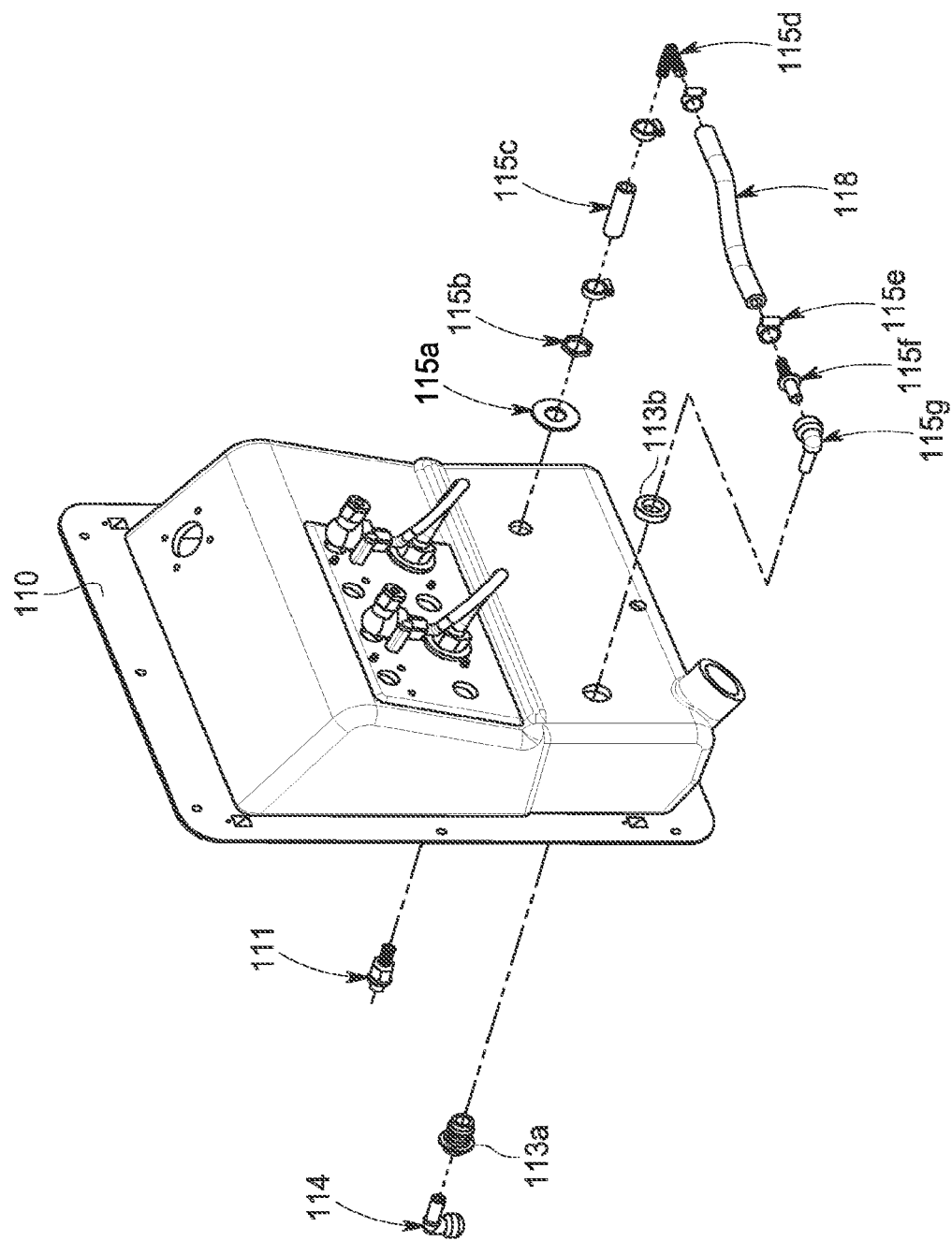
FIG. 11 is another perspective back view of an embodiment of a molded base of a wall box and valves or connectors.

FIG. 11 illustrates a back perspective view of a molded base 110, and the dialysis waste connector components used to collect and then dispose of waste dialysis fluids. The waste connector components include, in part, a waste connector fitting 111, connector tubing 112, and drain fittings 113a and 113b, drain elbow 114, and connecting components 115a-115g. The drain fittings lead into a covered waste compartment. The covered waste compartment prevents inadvertent or undesired patient or technician contact with waste dialysis fluids.

Figure 12:
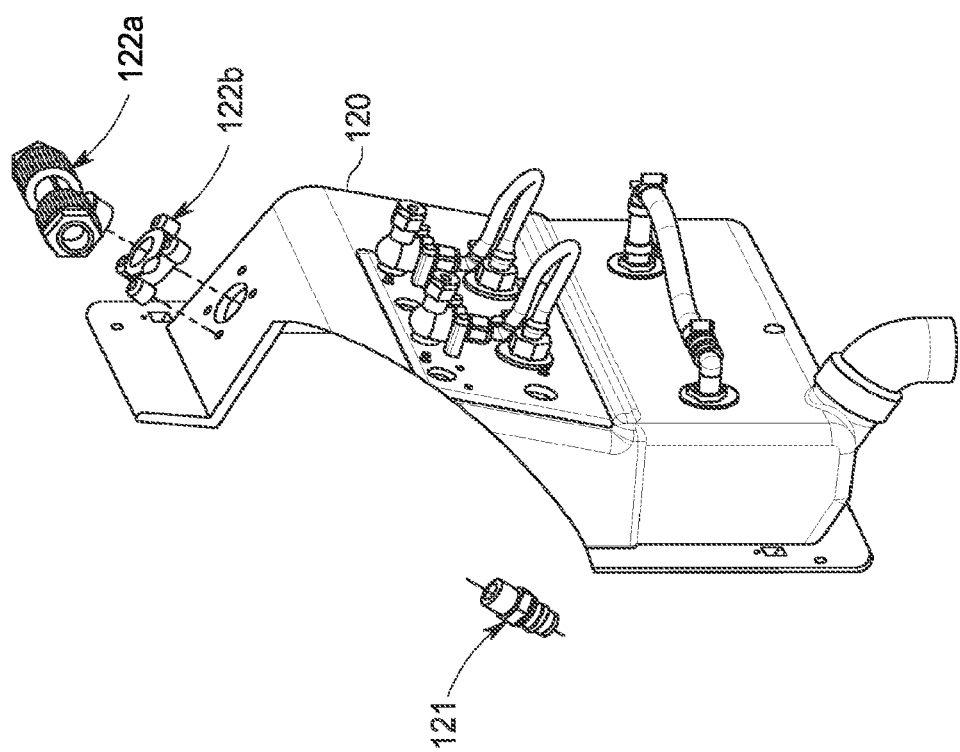
FIG. 12 is a cut-away perspective view of an embodiment of a molded base of a wall box, an inlet and out for reverse osmosis water, and valves and connectors for dialysis fluids and waste fluids.

FIG. 12 illustrates a cut-away perspective view of a molded base 120, and the RO water valve 121 and connectors 122a and 122b.

Figure 13:
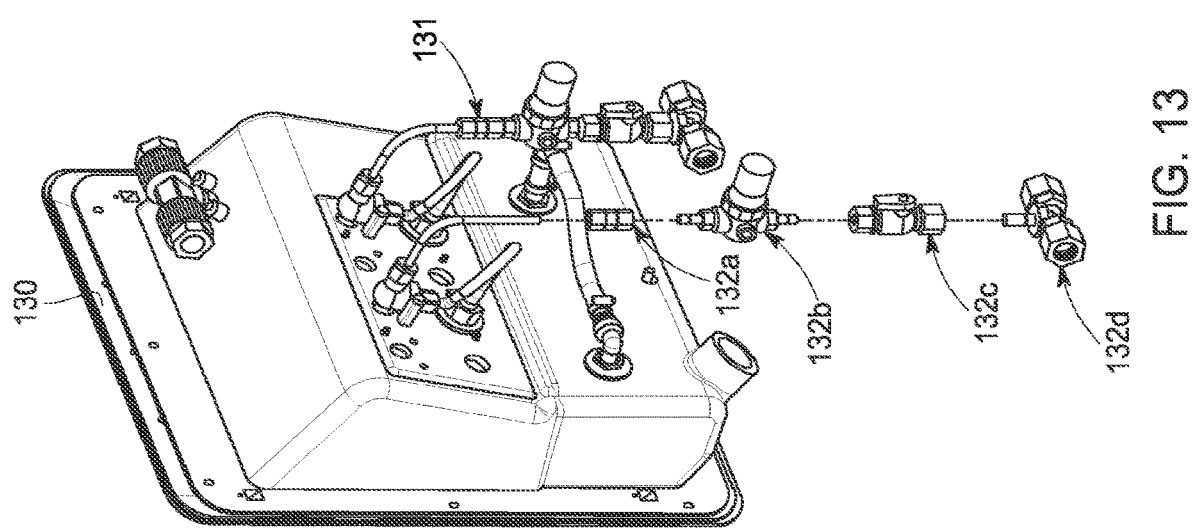
FIG. 13 is another perspective back view of an embodiment of a molded base of a wall box, an inlet and out for reverse osmosis water, and valves and connectors for dialysis fluids and waste fluids.

FIG. 13 illustrates a back perspective view of the dialysis fluids connectors and fittings. In this embodiment, primary and secondary acid solutions are connected to a molded base 130 the wall box. Dialysis acid solution regulator assembly 131 is connected to a primary acid port. The various components of an acid solution regulator assembly that would be connected to a secondary acid part include illustrated components 132a-132d.

Figure 14:
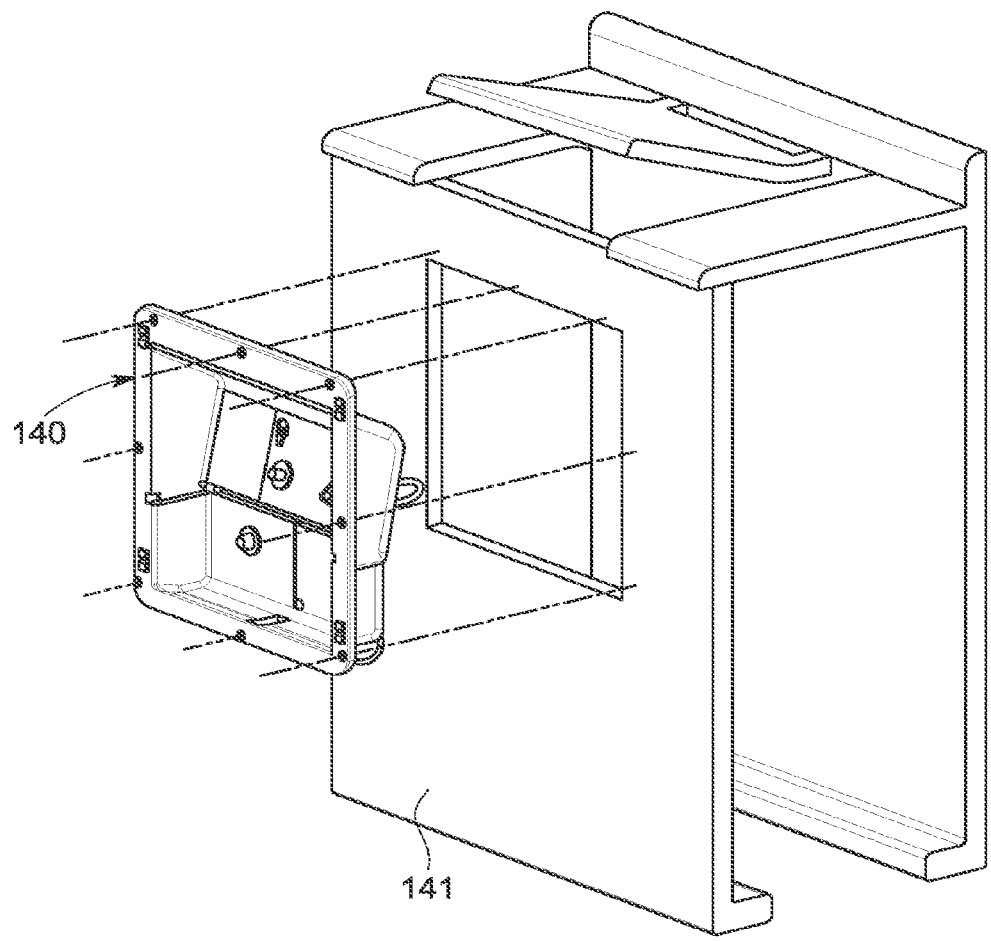
FIG. 14 is an exploded perspective view of a mounting cabinet and wall box of this disclosure.

FIG. 14 illustrates an embodiment of this disclosure having a wall box installed or mounted in a cabinet. Alternatively, the wall box may be installed or mounted in wall (not shown) or other suitable enclosure.

Figure 15:
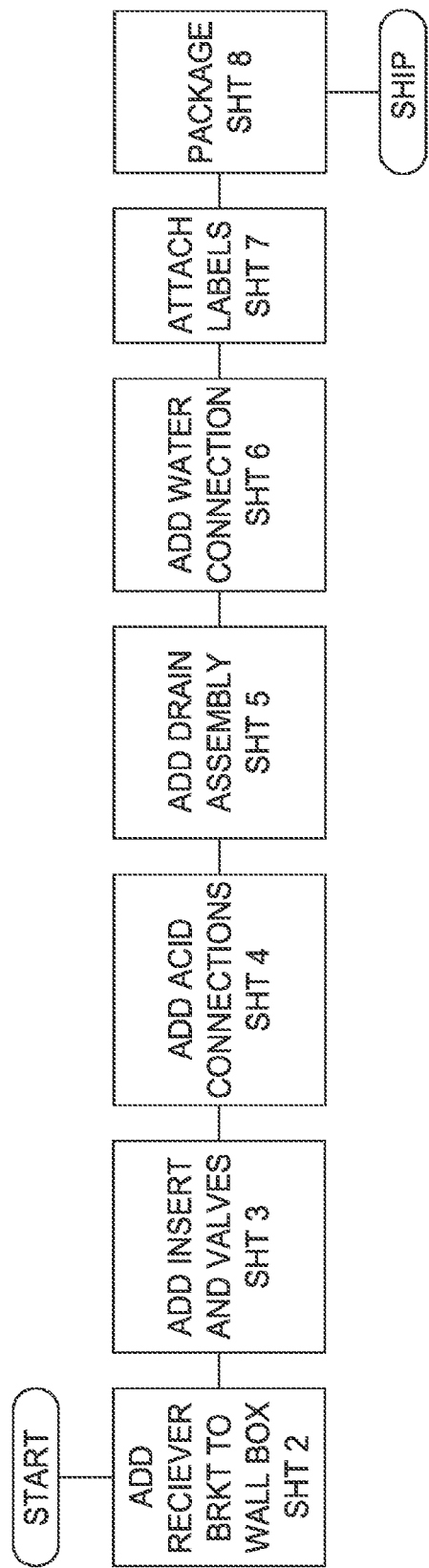
FIG. 15 is a flow chart of assembly steps for an embodiment of a wall box of this disclosure.

FIG. 15 illustrates a schematic diagram for assembling the components of a wall box of this disclosure for sale and distribution. The assembly steps include adding a receiver bracket to wall, adding valves, adding dialysis fluid connectors, adding waste fluid and drain assembly and RO water connection, adding labels, packaging, and shipping.

What is claimed:

1. A wall box for hemodialysis interface comprising at least two isolated zones,
   a first clean interface zone comprising sources of purified water and one or more dialysis fluids, and
   a second waste interface zone comprising one or more waste connectors and a waste drain,
   a divider separating a waste connector section from a waste drain section, and
   a cover enclosing the waste drain section.

2. The wall box of claim 1, wherein the first clean interface zone comprises a reverse osmosis water input and a reverse osmosis water outlet, and an inlet for one or more dialysis fluids and an outlet for one or more dialysis fluids.

3. The wall box of claim 2, wherein the first clean interface zone comprises one or more inlets and outlets for a bicarbonate solution, a primary acid solution, a secondary acid solution or a tertiary acid solution.

4. The wall box of claim 2, wherein the inlets and outlets comprise valves.

5. The wall box of claim 1, wherein the second waste interface zone further comprises a covered enclosure for the waste drain.

6. The wall box of claim 1 comprising a molded base fitted with apertures for reverse osmosis water and one or more dialysis fluids valves, a plurality of valves and connectors, a horizontal divider separating the isolated clean interface zone from the isolated waste interface zone.

7. The wall box of claim 6 further comprising a bezel fitted to the perimeter of the molded base.

8. The wall box of claim 6 further comprising a cover plate for the valves or connectors.

9. The wall box of claim 1, wherein the waste connector receives waste fluid from a dialysis machine.

10. The wall box of claim 1, wherein the wall box is impregnated with an anti-microbial product to inhibit bacterial growth.

* * * * *